(12) United States Patent
Jung et al.

(10) Patent No.: US 11,064,315 B2
(45) Date of Patent: Jul. 13, 2021

(54) METHOD OF GENERATING EXERCISE RELATED COMMUNITY AND ELECTRONIC DEVICE FOR PROVIDING SAME

(71) Applicant: Samsung Electronics Co., Ltd., Gyeonggi-do (KR)

(72) Inventors: Heejae Jung, Gyeonggi-do (KR); Junghwan Kim, Seoul (KR); Jungho Seo, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 1529 days.

(21) Appl. No.: 14/866,443

(22) Filed: Sep. 25, 2015

(65) Prior Publication Data
US 2016/0094959 A1 Mar. 31, 2016

(30) Foreign Application Priority Data

Sep. 26, 2014 (KR) .......................... 10-2014-0129486

(51) Int. Cl.
| | |
|---|---|
| *G06F 17/40* | (2006.01) |
| *H04W 4/08* | (2009.01) |
| *G16H 10/60* | (2018.01) |
| *G06Q 10/06* | (2012.01) |
| *G06Q 50/00* | (2012.01) |
| *G01S 19/19* | (2010.01) |

(52) U.S. Cl.
CPC .......... *H04W 4/08* (2013.01); *G06Q 10/0639* (2013.01); *G06Q 50/01* (2013.01); *G16H 10/60* (2018.01); *G01S 19/19* (2013.01)

(58) Field of Classification Search
CPC .......... G06F 17/40; H04L 51/32; G06Q 50/22
USPC ...................... 482/8; 709/205; 705/2, 3, 14.1
See application file for complete search history.

(56) References Cited

U.S. PATENT DOCUMENTS

| | | | |
|---|---|---|---|
| 8,597,093 B2 | 12/2013 | Engelberg et al. | |
| 9,323,868 B2* | 4/2016 | Balakrishnan | .......... G06F 17/40 |
| 9,769,107 B2* | 9/2017 | Marti | ...................... H04L 51/32 |
| 2014/0067494 A1* | 3/2014 | Squires | ............. G06Q 30/0269 |
| | | | 705/14.1 |

FOREIGN PATENT DOCUMENTS

| | | |
|---|---|---|
| KR | 10-2013-0097235 A | 9/2013 |
| KR | 10-2014-0061592 A | 5/2014 |
| KR | 10-1392708 A | 5/2014 |

OTHER PUBLICATIONS

Google patents search, Feb. 16, 2019 (Year: 2019).*

(Continued)

*Primary Examiner* — Dilek B Cobanoglu

(57) ABSTRACT

A host device includes: a data management module for receiving exercise data from an electronic device; a group management module for generating a group requiring preset conditions and determining whether to include the electronic device in the group based on whether the exercise data of the electronic device received from the data management module meets the conditions; and a league management module for, when the number of generated groups is two or more, controlling a configuration of the two or more groups based on a result of the determination on whether one or more electronic devices included in each of the two or more groups meet conditions required by the group whenever a preset period elapses.

16 Claims, 9 Drawing Sheets

(56) References Cited

OTHER PUBLICATIONS ip.com search, Mar. 5, 2021 (Year: 2021).*
Office Action dated Feb. 22, 2021 in connection with Korean Patent Application No. 10-2014-0129486, 12 pages.

* cited by examiner

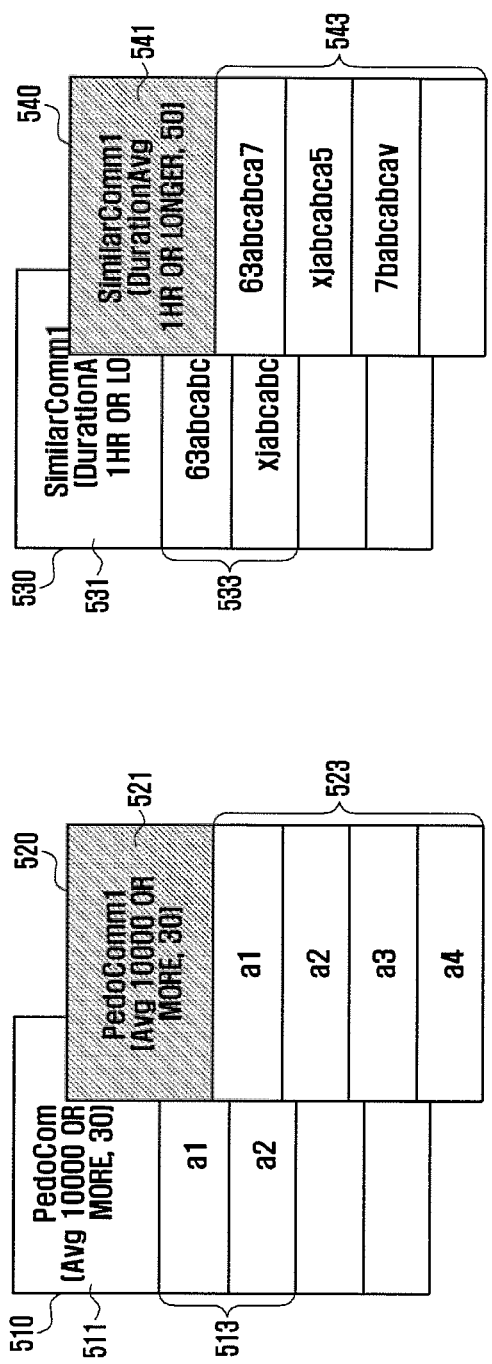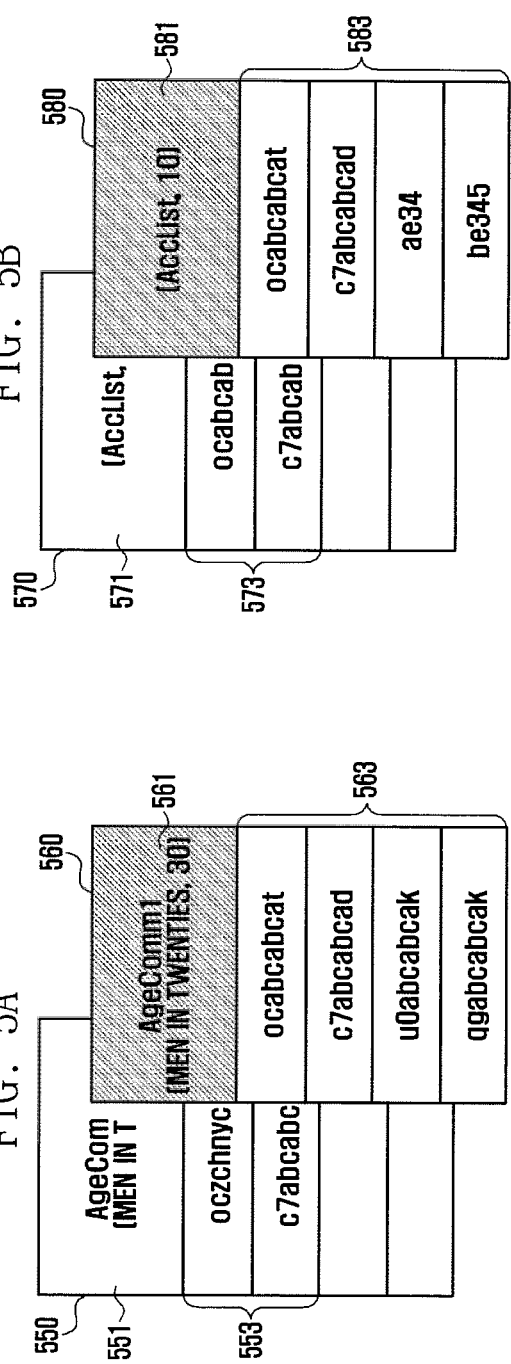
FIG. 5A  FIG. 5B  FIG. 5C  FIG. 5D

METHOD OF GENERATING EXERCISE RELATED COMMUNITY AND ELECTRONIC DEVICE FOR PROVIDING SAME

CROSS-REFERENCE TO RELATED APPLICATION AND CLAIM OF PRIORITY

The present application is related to and claims benefit under 35 U.S.C. § 119(a) of Korean Patent Application No. 10-2014-0129486, filed on Sep. 26, 2014, which is hereby incorporated by reference for all purposes as if fully set forth herein.

TECHNICAL FIELD

The present disclosure relates generally to a method of generating an exercise related communication and an electronic device for providing the same and, more particularly, to a method of generating a community based on exercise data and an electronic device for providing the same.

BACKGROUND

On the strength of an increase in civilized life conditions and a well-being trend over the society at large, interests in people's health are increasing gradually. In the health-related market, people's demands for identifying a health state using various health measurement devices has recently increased based on such interests. Accordingly, in order to meet the gradually increasing demands, various devices for measuring people's health are released in the health-related market. For example, the devices for measuring health include a blood pressure measuring device, a pulse measuring device, an exercise quantity measuring device, a skin current measuring device, and a body temperature measuring device, and such health measuring devices are installed and used in a portable terminal.

Further, users of the electronic devices use a health application to check their own health states. The health application analyzes exercise data updated in real time by the user of the electronic device and provides a service for burnt calories and menus.

SUMMARY

When a user uses a health-related application, the application calculates only ranks of users who use the corresponding application and provides a service to the users. This causes difficulty in securing reliability of data and meeting needs of the user when the user uses only a particular application.

The user of the electronic device may share only exercise data of acquaintances of the user of the electronic device (for example, other electronic devices registered to share particular information with the user of the electronic device through a friend service) when using a health-related application. This causes difficulty due to a limitation in securing data since the user of the electronic device can use only limited data.

The electronic device or an operator of a server identifies electronic devices which meet similar exercise data and generate a community in which the identified electronic devices are grouped. This provides cumbersomeness to the operator who generates the community since the operator who generates the community should manage the community at predetermined time intervals.

To address the above-discussed deficiencies, it is a primary object to provide a method of generating an exercise-related community and an electronic device for providing the same, which can solve the above problems.

Certain embodiments of the present disclosure include a method of generating a group by a host device is provided. The method includes: receiving exercise data from an electronic device by a data management module; generating a group requiring preset conditions by a group management module; determining whether to include the electronic device in the group based on whether the exercise data of the electronic device received from the data management module meets the conditions by the group management module; and when the number of generated groups is two or more, controlling a configuration of the two or more groups based on a result of the determination on whether one or more electronic devices included in each of the two or more groups meet conditions required by the group whenever a preset period elapses by the group management module.

An electronic device according to various embodiments of the present disclosure can use health-related data provided by two or more health applications, thereby further increasing reliability of the data.

An electronic device according to various embodiments of the present disclosure can automatically generate a community when exercise records of the electronic device are synchronized, thereby increasing convenience of the user of the electronic device.

A host device (for example, an electronic device or a server) according to various embodiments of the present disclosure can automatically provide and manage a community, thereby increasing convenience of the health application for the user of the electronic device and a participation motive of the user.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

The above and other objects, features and advantages of the present disclosure will be more apparent from the following detailed description in conjunction with the accompanying drawings, in which: For a more complete understanding of the present disclosure and its advantages, reference is now made to the following description taken in conjunction with the accompanying drawings, in which like reference numerals represent like parts:

FIGS. 5A, 5B, 5C, and 5D (together referred to as FIG. 5) illustrate the group generation by the host device according to various embodiments of the present disclosure;

DETAILED DESCRIPTION

Figure 1:
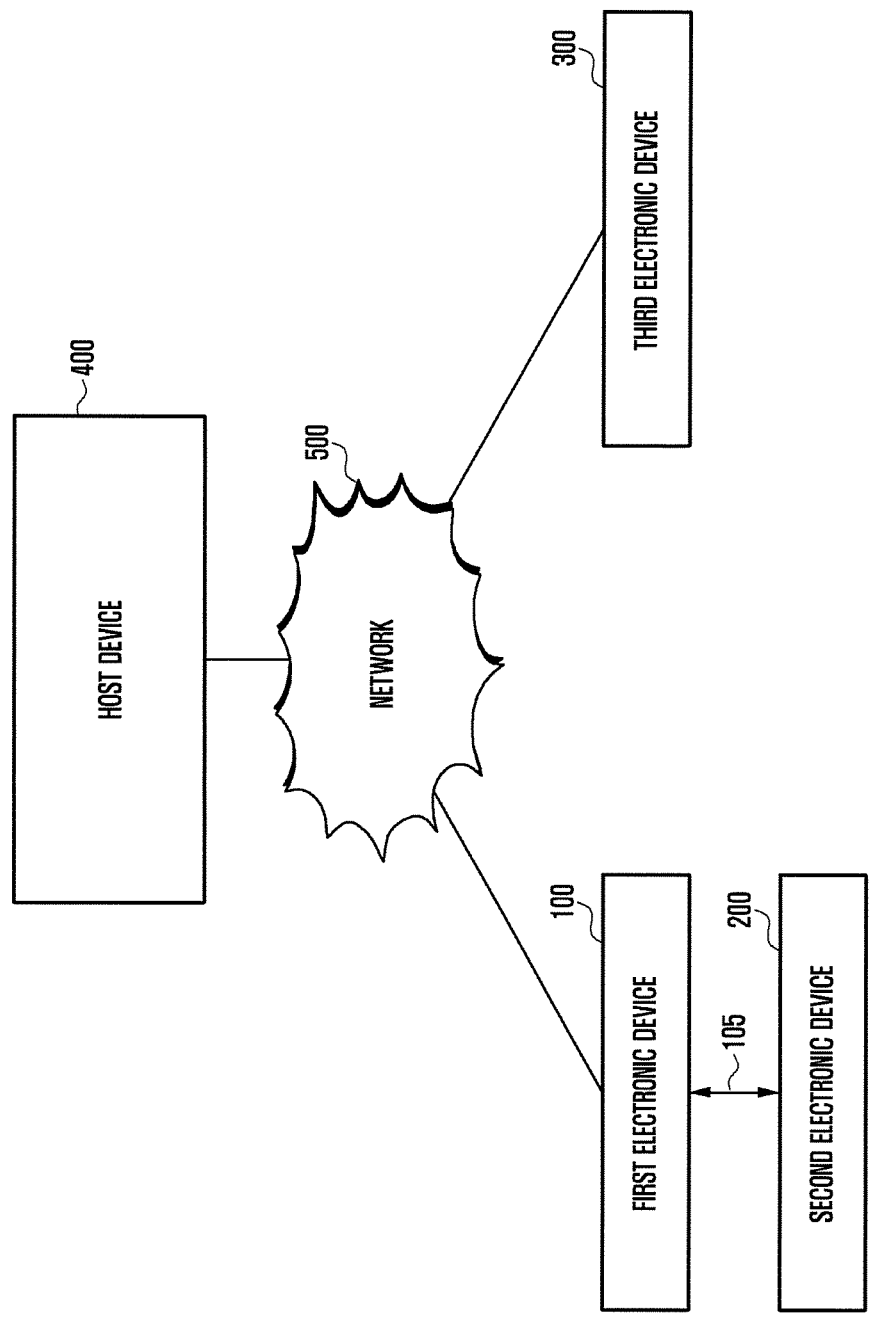
FIG. 1 illustrates a connection between a host device and electronic devices through a network according to various embodiments of the present disclosure.

FIGS. 1 through 8, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged wireless communication system. Hereinafter, various embodiments will be described in detail with reference to the accompanying drawings. It should be noted that the same elements will be designated by the same reference numerals although they are shown in different drawings. Further, a detailed description of a known function and configuration which may make the subject matter of the present disclosure unclear will be omitted. Hereinafter, it should be noted that only the descriptions will be provided that may help understanding the operations provided in association with the various embodiments of the present disclosure, and other descriptions will be omitted to avoid making the subject matter of the present disclosure rather unclear.

FIG. 1 illustrates a connection between a host device 400 and electronic devices 100, 200, and 300 through a network 500 according to various embodiments of the present disclosure.

The first electronic device 100 may communicate with the second electronic device 200. The first electronic device 100 and the third electronic device 300 may be connected to the host device 400 through the network 500. Two or more electronic devices may be connected through the network 500, and a single electronic device 300 may be connected to the host device 400 through the network 500.

In this disclosure, an electronic device 100, 200, 300 may be a device that performs a communication function. For example, an electronic device 100, 200, 300 may be a smart phone, a tablet PC (Personal Computer), a mobile phone, a video phone, an e-book reader, a desktop PC, a laptop PC, a netbook computer, a PDA (Personal Digital Assistant), a PMP (Portable Multimedia Player), an MP3 player, a portable medical device, a digital camera, or a wearable device (e.g., an HMD (Head-Mounted Device) such as electronic glasses, electronic clothes, an electronic bracelet, an electronic necklace, an electronic appcessory, an electronic tattoo or a smart watch).

The electronic device 100 according may perform the same functions or operations as other electronic devices 200 and 300. The host device 400 may be a server, a device performing the same function as that of the electronic device 100, or a computer including a database (DB).

The electronic devices 100, 200, and 300 may be the same type or different types of devices. For example, the first electronic device 100 may be a smart phone and the second electronic device 200 may be a wearable device.

The first electronic device 100 according to an embodiment of the present disclosure may transmit data to or receive data from the second electronic device 200 through short range communication 105 (for example, Bluetooth communication, Near Field Communication (NFC), Infrared Data Association (IrDA)).

The first electronic device 100 may receive data related to exercise from the second electronic device 200 which is the wearable device. For example, a user of the second electronic device 200 may generate exercise-related data measured through the second electronic device 200. The exercise-related data may be data on a quantity of exercise of the user, heart rate data, data on the number of steps, calorie data, sleep data, movement distance data. The second electronic device 200 according to an embodiment may store the measured exercise-related data.

The first electronic device 100 according to an embodiment of the present disclosure may receive raw data on exercise from the second electronic device 200, which is the wearable device. The raw data may be data generated by measuring the quantity of exercise of the second electronic device 200 by the second electronic device 200. For example, the raw data may be data on the number of steps per week or a movement distance of the second electronic device 200. Additionally, for example, the raw data may be data measured through a sensor without the application of a predetermined calculation formula to calculate calorie data.

The first electronic device 100 according to an embodiment of the present disclosure may receive an application from the host device 400. The first electronic device 100 according to an embodiment may receive an application installation file from the host device 400 and may install the application according to the execution of the application installation file. The first electronic device 100 may execute the installed application and input ID information and password information of the electronic device 100 so as to register the first electronic device 100 in the host device 400.

The first electronic device 100 according to an embodiment of the present disclosure may receive an application, which provides a health service, from the host device 400, and then install the application. The electronic device 100 may register the electronic device 100 in the host device 400 by inputting ID information and password information into the executed application and then transmitting the information to the host device 400.

The first electronic device 100 according to an embodiment of the present disclosure may transmit exercise data to the host device 400. The first electronic device 100 may transmit exercise data received from the second electronic device 200, which is the wearable device, to the host device 400. The first electronic device 100 according to an embodiment may transmit exercise data measured and stored by the first electronic device 100 itself to the host device 400. For example, the first electronic device 100 may measure and store step data of the user of the first electronic device 100 and movement distance data detected through a motion sensor or a GPS sensor. Additionally, for example, the first electronic device 100 may transmit weight data and height data to the host device 400.

The first electronic device 100 according to an embodiment of the present disclosure may transmit exercise-related data included in an application, which is not supported by the host device 400, to the host device 400. For example, the first electronic device 100 may install and use two or more health-related applications and store exercise-related data corresponding to each of the applications. The first electronic device 100 may transmit exercise-related data of another application stored in a storage module 120 to the host device 400. For example, when the host device 400 supports an A health application, the first electronic device 100 may transmit exercise-related data included in a B health application to the host device 400.

The third electronic device 300 according to an embodiment of the present disclosure may transmit exercise data measured by the third electronic device 300 to the host device 400. For example, the third electronic device 300 may measure, store, and transmit step data or movement distance data detected by a user of the third electronic device 300 through a motion sensor or a GPS sensor.

The host device 400 according to an embodiment of the present disclosure may receive a signal making a request for installation of an application that provides a health service from the first electronic device 100. The host device 400 may transmit the application to the first electronic device 100 in response to the signal received from the first electronic device 100.

The host device 400 according to an embodiment of the present disclosure may receive exercise data from the first electronic device 100 and the third electronic device 300. The host device 400 according to an embodiment may store the received exercise data. The host device 400 may calculate the received exercise data based on a pre-stored calculation method. For example, the host device 400 may receive raw data such as movement distance data of the first electronic device 100 or data on the number of steps per hour from the first electronic device 100.

The host device 400 according to an embodiment of the present disclosure may calculate burnt calorie data and an obesity rate of the first electronic device 100 by applying a predetermined calculation method to the received raw data. The host device 400 according to an embodiment may perform recalculation by extracting only raw data (for example, movement distance data and step data) among exercise-related data included in other applications and applying a predetermined calculation method.

The host device 400 according may receive exercise-related data included in other applications through an interworking with an external server that provides the other applications.

The host device 400 according to an embodiment of the present disclosure may generate a group requiring preset conditions. The preset conditions may be weight data, height data, data on the number of steps, burnt calorie data, age data, gender data, and data on the type of electronic device which measures the exercise data. The host device 400 according to an embodiment may determine whether the exercise data of the first electronic device 100 meets the preset conditions. When it is determined that the first electronic device 100 meets the preset conditions, the host device 400 may determine to include the first electronic device 100 in a group which meets the conditions.

The host device 400 according to an embodiment of the present disclosure may transmit a signal making a request for joining the group to the first electronic device 100. When the host device 400 receives an acknowledgment response signal with respect to the signal transmitted from the first electronic device 100, the host device 400 may determine to allow the first electronic device 100 to join the group. When the preset condition is met, the host device 400 according to an embodiment may transmit a request signal to the first electronic device 100, the second electronic device 200, and the third electronic device 300.

The host device 400 according to an embodiment of the present disclosure may transmit a request signal to the first electronic device 100 when a condition about the number of people among the preset conditions is met. For example, the host device 400 may set the conditions of the group as five and 10000 steps or more per week. The host device 400 may identify electronic devices which have exercise data including 10000 steps or more per week. When the number of identified electronic devices is five corresponding to the preset condition about the number of people, the host device 400 may transmit request signals to the five electronic devices. When the preset condition about the number of people is not met, the host device 400 according to an embodiment may not transmit the group request signal to the electronic devices which meet the exercise data condition.

The network 500 according to an embodiment of the present disclosure may be a telecommunication network. The telecommunication network may include at least one of a computer network, Internet, Internet of Things, and a telephone network.

Figure 2:
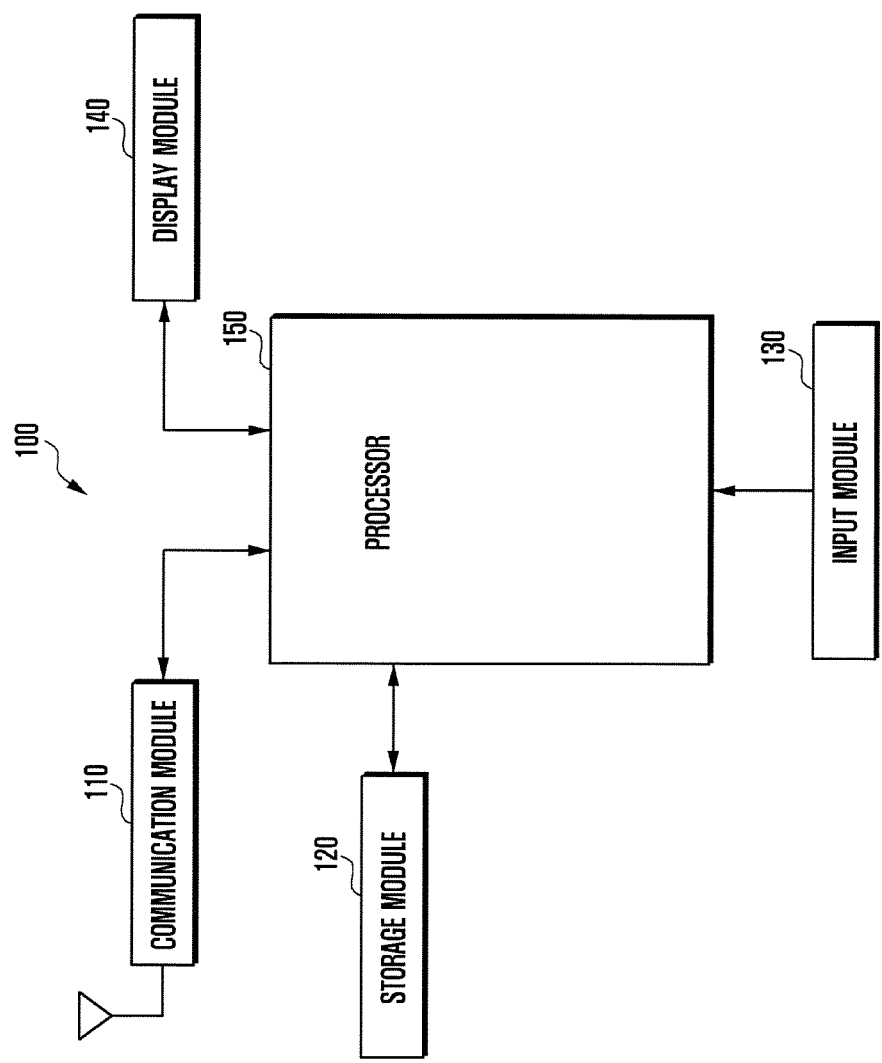
FIG. 2 illustrates a configuration of the electronic device according to various embodiments of the present disclosure.

FIG. 2 illustrates a configuration of the electronic device 100 according to various embodiments of the present disclosure. The first electronic device 100 may be named the electronic device 100 for the convenience of description.

The electronic device 100 may include a communication module 110, a storage module 120, an input module 130, a display module 140, and a processor 150.

The communication module 110 is a communication module for supporting a mobile communication service of the electronic device 100. The communication module 110 may form a communication channel with a mobile communication system. To this end, the communication module 110 may include a radio frequency transmitter for up-converting and amplifying a frequency of a transmitted signal and a receiver for low-noise amplifying a received signal and down-converting a frequency thereof.

The communication module 110 according to an embodiment of the present disclosure may perform short range communication (for example, Bluetooth communication) with the second electronic device 200. For example, the second electronic device 200 is a wearable device, and the second electronic device 200 corresponding to the wearable device may generate health data (for example, heart rate data, data on the number of steps, calorie data, sleep data, distance data, location data, and path data) detected by the user. The communication module 110 according to an embodiment may receive heart rate data, data on the number of steps, calorie data, sleep data, and distance data from the wearable device.

The storage module 120 may store an application program for reproducing various stored files, and a key map or a menu map for operating the display module 140 as well as an application program required for operating functions according to embodiments of the present disclosure. Each of the key map and the menu map may have various forms.

That is, the key map may be a keyboard map, a 3×4 key map, a qwerty key map, or a control key map for controlling the operation of a currently activated application program. Further, the menu map may be a control key map for controlling the operation of the currently activated application program. In addition, the menu map may also be a menu map for controlling the operation of the currently activated application program or a menu map having various menu items provided by the electronic device 100. The storage unit 120 may largely include a program area and a data area.

The program area may store an Operating System (OS) for booting the electronic device 100 and operating each of the aforementioned components, an application program for reproducing various files, for example, an application for supporting a call function according to whether the function of the electronic device 100 is supported, a web browser for accessing an Internet server, an MP3 application program for reproducing other sound sources, an image output application program for reproducing pictures, and a video reproduction application program.

The data area may be an area in which data generated according to the use of the electronic device 100 is stored, and may store one or more icons and various contents according to phone book information or a widget function. Further, when the data area is implemented in the display module 410, the data area may store a user input made through the display module 140.

The input module 130 may include a plurality of input keys and function keys for receiving number or character information and setting various functions. The function keys may include a direction key, a side key, and a shortcut key, which are set to execute particular functions. Further, the input module 130 may generate a key signal related to a user setting and a control of the function of the electronic device 100 and transmit the generated key signal to the controller 160.

The display module 140 may display information input by the user or information to be provided to the user as well as various menus of the electronic device 100. That is, the display module 140 may provide various screens according to the use of the electronic device, for example, a standby screen, a menu screen, a message entering screen, and a call screen. The display module 140 may be implemented by a Liquid Crystal Display (LCD) or an Organic Light Emitted Diode (OLED), and may be included in an input means. Further, the electronic device 100 may provide various menu screens based on the display module 140 according to the supporting of the display module 140.

The display module 140 may be combined with a touch panel and provided in the form of touch screen. For example, the touch screen may include an integral module in which a display panel and a touch panel are coupled to each other in a stack structure. The touch panel may recognize a touch input in at least one of, for example, a capacitive type, a resistive type, an infrared type, or ultrasonic type. Also, the touch panel may further include a controller (not illustrated). In case of a capacitive type, a physical contact or proximity may be recognized. The touch panel may further include a tactile layer. In this case, the touch panel may offer a tactile feedback to a user.

The display module 140 according to an embodiment may detect a touch input event making a request for performing the function of the electronic device 100. The display module 140 may transfer information corresponding to the detected touch input event to the processor 150.

The processor 150 may support execution of an initialization process by controlling power supply to each of the components of the electronic device 100, and control each of the components when the initialization process is completed.

The processor 150 according to an embodiment of the present disclosure may control the communication module 110 to transmit exercise data to the host device 400. The exercise data may be data received from another electronic device (for example, a wearable device or the second electronic device 200) or data measured and stored by the electronic device 100.

The electronic device 100 according to an embodiment of the present disclosure may measure exercise-related data on the user of the electronic device 100 through a GPS module (not shown) or a motion sensor (not shown). For example, the electronic device 100 may measure and generate distance data and location data on the user of the electronic device 100 through the GPS module. Additionally, for example, the electronic device 100 may measure and generate step data and movement distance data on the user of the electronic device 100 through the motion sensor.

The processor 150 according to an embodiment of the present disclosure may control the communication module 110 to transmit exercise data included in an application, which is not supported by the host device 400, to the host device 400. For example, the processor 150 may control the communication module 110 to transmit exercise-related data (for example, step data and movement distance data) stored in the storage module 120 to the host device 400. Additionally, for example, the processor 150 may control the communication module 110 to transmit exercise-related data included in application B rather than application A, which is supported by the host device 400, to the host device 400.

When the processor 150 according to an embodiment of the present disclosure receives a signal indicating whether to join a group from the host device 400, the processor 150 may display a group join UI through the display module 140. The processor 150 may determine whether to join the group based on a user input event for the group join UI displayed through the display module 140.

When the processor 150 according to an embodiment of the present disclosure detect a user input indicating the group join, the processor 150 may control the communication module 110 to transmit an acknowledge signal of the group join to the host device 400. The acknowledge signal of the group join may be a consent signal with respect to all services (for example, a league service and a friend service) provided by the host device 400.

The processor 150 according to an embodiment of the present disclosure may receive information on the league service including two or more groups from the host device 400. The league service may be a service supported by the host device 400, and includes a service for controlling a configuration of electronic devices included in the group based on a result of the determination on whether the electronic device included in each of the groups meets conditions required by the corresponding group whenever a preset period elapses.

The processor 150 according to an embodiment may receive information related to start, renewal, and end of the league service from the host device 400. For example, the processor 150 may receive data from the host device 400 at a time when the league service starts, at every time when the league service is renewed after a preset period, or at a time when the league service ends. For example, the processor 150 may receive a notification signal from the host device 400 when the league service starts, is renewed, and ends. The processor 150 may display a UI corresponding to the notification signal through the display module 140.

The processor 150 according to an embodiment may receive information on a group changed based on a result according to whether a condition required by the group is met whenever a preset period elapses from the host device 400. For example, when a preset period (for example, 7 days or 15 days) set by the host device 400 elapses, if the user of the electronic device 100 included in a first group does not meet the condition required by the corresponding group, the electronic device 100 may be changed to be included in a second group. The electronic device 100 may receive information informing that the group including the electronic device 100 is changed to the second group from the host device 400.

Figure 3:
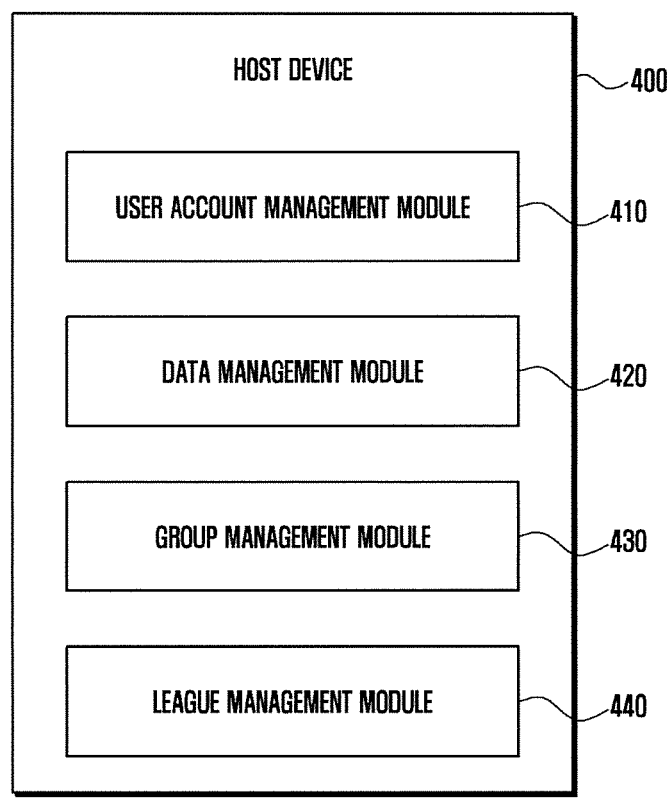
FIG. 3 illustrates a configuration of the host device according to various embodiments of the present disclosure.

FIG. 3 illustrates a configuration of the host device 400 according to embodiments of the present disclosure.

The host device 400 according to an embodiment of the present disclosure may include a user account management module 410, a data management module 420, a group management module 430, and a league management module 440.

The user account management module 410 according to an embodiment of the present disclosure may store ID information and password information of the electronic device 100, and the type of wearable device of the electronic device 100. For example, the electronic device 100 may receive an application that provides an exercise service from the host device 400, and may input the ID information to use the exercise service provided from the host device 400 after executing the received exercise application. The user account management module 410 may store ID information, password information, and the type of exercise data measurement device input by the user of the electronic device 100.

The data management module 420 according to an embodiment of the present disclosure may receive exercise data from the electronic device 100. The data management module 420 according to an embodiment may transmit exercise data of the electronic device 100 received through a communication unit (not shown) to the data management module 420.

The data management module 420 according to an embodiment of the present disclosure may receive the exercise data of the electronic device 100 through an interworking with another host device as well as the service supported by the host device 400. For example, the user of the electronic device 100 may install and use a separate application that provides another exercise service as well as the exercise service provided by the host device 400. The data management module 420 according to an embodiment may receive exercise data used in a separate application stored in the storage module 120 of the electronic device 100.

The data management module 420 according to an embodiment of the present disclosure may calculate the exercise data received from the electronic device 100 based on a calculation method pre-stored in the host device 400. For example, the data management module 420 may receive raw data related to the exercise of the electronic device 100 from the electronic device 100. The raw data related to the exercise may be data measured by the exercise of the user of the electronic device 100. For example, the raw data related to the exercise may be inherent data such as movement distance data, exercise period data, or step distance data measured through a sensor (for example, a GPS sensor, a motion sensor, or a wearable device) without the application of a calculation formula.

The data management module 420 according to an embodiment may calculate raw data related to the exercise of the electronic device 100 based on the calculation method pre-stored in the host device 400. The data management module 420 according to an embodiment may calculate calorie data, weight loss request data, obesity rate data, and data on a quantity of exercise per hour based on the raw data related to the exercise.

The data management module 420 according to an embodiment may transmit the calculated exercise data to the group management module 430.

The group management module 430 according to an embodiment of the present disclosure may generate a group requiring preset conditions. The preset conditions may be at least one of data on the number of steps, burnt calorie data, age data, gender data, the type of electronic device measuring the exercise data (for example, a portable terminal or a wearable device), and data on the number of people. For example, the group management module 430 may generate a group having conditions of 10000 steps or more per week and women in her thirties or older.

The group management module 430 according to an embodiment may determine data similarity through analysis of the exercise data. The group management module 430 may generate conditions according to the determined data similarity. For example, when people who exercise in similar paths (for example, within an error range 100 m or 500 m) are detected through analysis of location data, the group management module 430 may add conditions for the location data and path data. The group management module 430 may generate a group based on the added conditions.

The group management module 430 according to an embodiment of the present disclosure may determine whether to include the electronic device 100 in the group based on a result of the determination on whether the exercise data of the electronic device 100 received from the data management module 420 meets preset conditions. For example, the group management module 430 may generate a group based on conditions 10000 steps or more per week and 30 people, and determine whether at least one piece of the exercise data received from the data management module 420 meets the conditions.

When it is determined that the exercise data of the electronic device 100 meets the conditions, the group management module 430 according to an embodiment of the present disclosure may transmit a signal making a request for joining the group to the electronic device 100. The group management module 430 according to an embodiment may transmit the group join request signal to the electronic device 100 only when the preset number of people is met. For example, the group management module 430 may generate a group requiring the conditions of 10000 steps or more per week and 30 people, and determine electronic devices having 10000 steps or more per week. When the determined electronic devices meet the condition of 30 people, the group management module 430 may transmit the group join request signal to the electronic devices of the 30 people.

When an acknowledge response signal is received in response to the signal transmitted from the electronic device 100, the group management module 430 according to an embodiment of the present disclosure may include the electronic device 100 in the group. When the electronic device 100 is included in the group, the group management module 430 may generate a separate ID corresponding to the electronic device 100 of the corresponding group. The separate ID may be different from a subscription ID. Each of the IDs of the electronic devices included in the group may be randomly determined and the ID of each of the electronic devices may be generated to be distinguished from that of another electronic device. Additionally, for example, IDs provided to the electronic device from respective groups may be different.

When the number of generated groups is two or more, the league management module 440 according to an embodiment of the present disclosure may control a configuration of two or more groups based on a result of the determination on whether at least one electronic device 100 included in each of the two or more groups meets conditions required by the group whenever a preset period elapses.

The preset period may be selected and changed by the league management module 440. For example, the preset period may be designated as every 7 days, 15 days, or 30 days. Additionally, for example, the preset period may be changed and renewed by the host device 400.

When the preset period elapses, the league management module 440 according to an embodiment of the present disclosure may renew a group to include the electronic device 100 based on a result of the determination on whether the electronic device 100 included in one of the two or more groups meets conditions required by the group. For example, the league management module 440 may identify whether electronic devices included in the group meet conditions required by the group every preset period. The league management module 440 may change the configuration of the electronic devices included in each of the groups based on a result of the identification of whether the conditions are met.

When the preset period elapses, the league management module 440 according to an embodiment of the present disclosure may classify the two or more groups according to whether the conditions required by the group are met.

For example, the type of group may include a first group and a second group, and the first group may be classified as a condition-met group and the second group may be classified as a condition-unmet group. When each of the first group and the second group corresponds to the group requiring the condition of 10000 steps or more for 7 days, if the electronic device 100 included in the first group has 6000 steps or more for 7 days, the group of the electronic device 100 is changed to the second group after a preset period elapses.

The league management module 440 according to an embodiment of the present disclosure may identify a group, which does not reach the number of times by which the preset condition is met, among the classified groups, and delete the identified group. For example, the league management module 440 may renew the configuration of the electronic devices included in the group according to whether the condition is met whenever a preset period lapses. The group, which does not reach the preset number of times (for example, two times, three times, or four times) corresponding to the condition required by the group may be deleted from the renewed groups. Additionally, for example, when the electronic device 100 does not meet the condition required by the group even though a preset period (for example, 7 days) elapses three times, the league management module 440 may delete the group including the electronic device 100.

When pieces of information on the number of times by which the condition required by respective groups of the classified groups is met are different from each other, the league management module 440 according to an embodiment of the present disclosure may end the controlling of the configuration of the group. The league management module 440 according to an embodiment may renew the type of group according to whether the condition is met whenever a preset period lapses. For example, when the league service operates with three groups such as a first group, a second group, and a third group, the league management module 440 may end the league service if the number of times by which the condition is met corresponds to three times in the first group, the number of times by which the condition is met corresponds to two times in the second group, and the number of times by which the condition is met corresponds to one time in the third group.

The league management module 440 according to an embodiment may control electronic devices included in the same group to use a friend service when the league service ends. The friend service may be a service in which a user of an electronic device selects another electronic device with which particular information is shared and shares the particular information with the selected electronic device.

When the preset period elapses, if all electronic devices included in the group meet the conditions required by the group, the league management module 440 according to an embodiment of the present disclosure may not control the configuration of the group which meets the conditions for the preset period. For example, when all electronic devices included in the group requiring particular conditions meet the corresponding conditions, the league management module 440 may maintain the configuration of the electronic devices included in the corresponding group for a preset period (for example, seven days).

The preset condition may be weight data, height data, burnt calorie data, age data, gender data, and data on the type of electronic device which measures the exercise data.

FIG. 4 illustrates the group generation by the host device 400 according to various embodiments of the present disclosure.

Figures 4A, 4B:
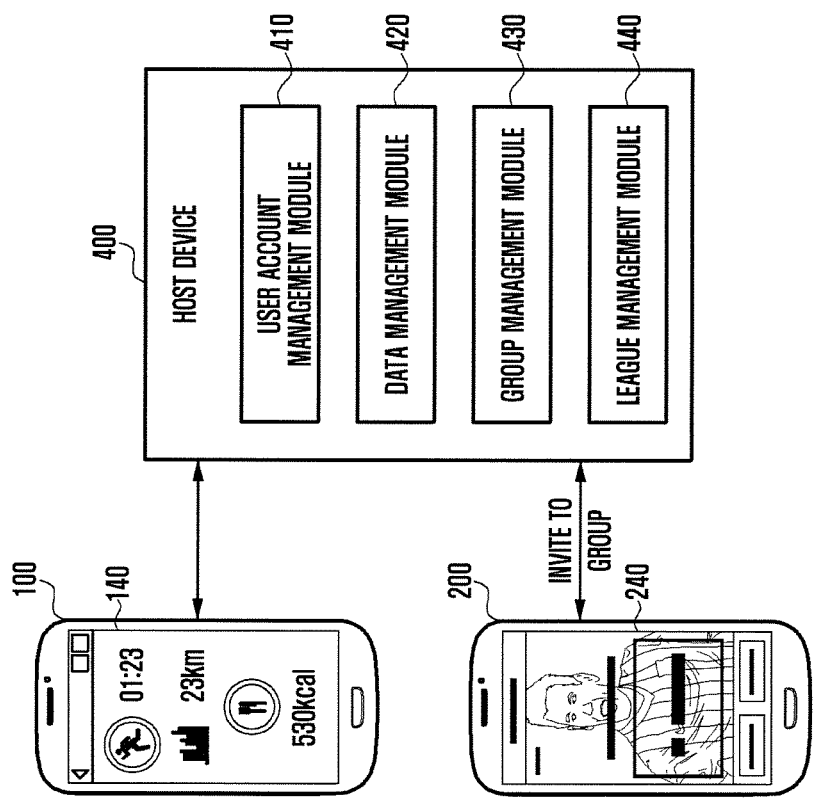
FIGS. 4A and 4B (together referred to as FIG. 4) illustrate the group generation by the host device according to various embodiments of the present disclosure.

As shown in FIG. 4A, the first electronic device 100 may transmit data to or receive data from the host device 400. The second electronic device 200 may transmit data to or receive data from the host device 400.

The first electronic device 100 according to an embodiment may receive an application from the host device 400 and install the received application. The first electronic device 100 according to an embodiment may transmit exercise-related data to the host device 400. The exercise-related data may be raw data stored in the first electronic device 100 (for example, movement distance data, location data, or step data).

When the exercise-related data is synchronized, the first electronic device 100 according to an embodiment may transmit the synchronized exercise-related data to the host device 400. The exercise-related data may be data measured by the first electronic device 100 or data received by another electronic device (for example, a wearable device).

The host device 400 according to an embodiment may automatically generate a group requiring preset conditions. The host device 400 may determine electronic devices corresponding to data which meets conditions based on the preset conditions. For example, when the electronic device corresponding to the data which meets the preset conditions is the second electronic device 200, the host device 400 may transmit a signal making a request for joining the group to the second electronic device 200.

As shown in FIG. 4B, the host device 400 may generate a table 403 based on the exercise-related data received from the electronic devices.

The host device 400 according to an embodiment may generate a table by using names of the electronic devices, ID account data corresponding to the electronic devices, the types of device measuring exercise data (for example, a wearable device of an S company, a portable terminal of an S company, and a wearable device of an A company).

The table according to an embodiment may store the name of each electronic device (for example, Naneunna, Kim Young Su, Lee Cheol Soo, Hong Gil Dong, and Park Ji Young). The table 403 according to an embodiment may store ID information corresponding to each name (for example, ME000, YS 123, CS342, and GD563, JY973). The table 403 according to an embodiment may store the devices such that the wearable device of the S company is called "1" and the wearable device of the A company is called "2".

FIG. 5 illustrates the group generation by the host device 400 based on conditions according to various embodiments of the present disclosure.

The host device 400 according to an embodiment of the present disclosure may generate a group according to preset conditions. As shown in FIG. 5A, the host device 400 may generate a group which requires the average number of steps per week and the number of people. For example, the host device 400 may generate a group having conditions of average steps of 10000 or more and 30 people. When the preset condition corresponding to the 30 people is not met, the host device 400 according to an embodiment may generate a temporary group 510 which meets a preset condition 511. The temporary group 510 may include electronic devices a1 and a2 513 corresponding to data which meets the average steps of 10000.

When the condition of the 30 people is met, the host device 400 may generate a group UI 520 including the preset condition 521. The group UI 520 may transmit a group join request signal to electronic devices a1, a2, a3, and a4 523 and the remaining electronic devices of 26 people that meet the condition.

As shown in FIG. 5B, the host device 400 may generate a group which requires a walking time and the number of people. For example, the host device 400 may generate a group having conditions of one hour of walking per week and 50 people. When the preset condition corresponding to the 50 people is not met, the host device 400 according to an embodiment may generate a temporary group 530 which meets a preset condition 531. The temporary group 530 may include electronic devices 63*abcabca*7 and xjabcabca5 533 corresponding to data which meets the condition of one hour of walking per week. The ID may be a random ID generated by the host device 400.

When the condition of the 50 people is met, the host device 400 may generate a group UI 540 including a preset condition 541. The group UI 540 may transmit a group join request signal to electronic devices 63*abcabca*7, xjabcabca5, and 7*babcabcav* 543 and the remaining electronic devices of 47 people which meet the condition.

As shown in FIG. 5C, the host device 400 may generate a group which requires a gender, an age and the number people. For example, the host device 400 may generate a group having conditions of men in their twenties and 30 people. When the preset condition corresponding to the 30 people is not met, the host device 400 according to an embodiment may generate a temporary group 550 which meets a preset condition 551. The temporary group 550 may include electronic devices ocabcabcat and c7*abcabcad* 553 corresponding to data which meets the condition of men in their twenties. The ID may be a random ID generated by the host device 400.

When the condition of the 30 people is met, the host device 400 may generate a group UI 560 including a preset condition 561. The group UI 560 may transmit a group join request signal to electronic devices ocabcabcat, c7*abcabcad*, u0*abcabcak*, and qgabcabcak 563 and the remaining electronic devices of 26 people which meet the condition.

As shown in FIG. 5D, the host device 400 may generate a group which requires the type of particular device measuring exercise data and the number people. For example, the host device 400 may generate a group having conditions of the type of electronic device measuring exercise data (for example, a wearable device of an S company and a wearable device of an A company) and 10 people. When the preset condition corresponding to the 10 people is not met, the host device 400 according to an embodiment may generate a temporary group 570 which meets a preset condition 571. The temporary group 570 may include electronic devices ocabcabcat and c7*abcabcad* 553 corresponding to data which meets the type of particular wearable device. The ID may be a random ID generated by the host device 400.

When the condition of the 10 people is met, the host device 400 may generate a group UI 580 including a preset condition 581. The group UI 580 may transmit a group join request signal to electronic devices ocabcabcat, c7*abcabcad*, ae34, and be345 and the remaining electronic devices of 6 people which meet the condition.

Figure 6A:
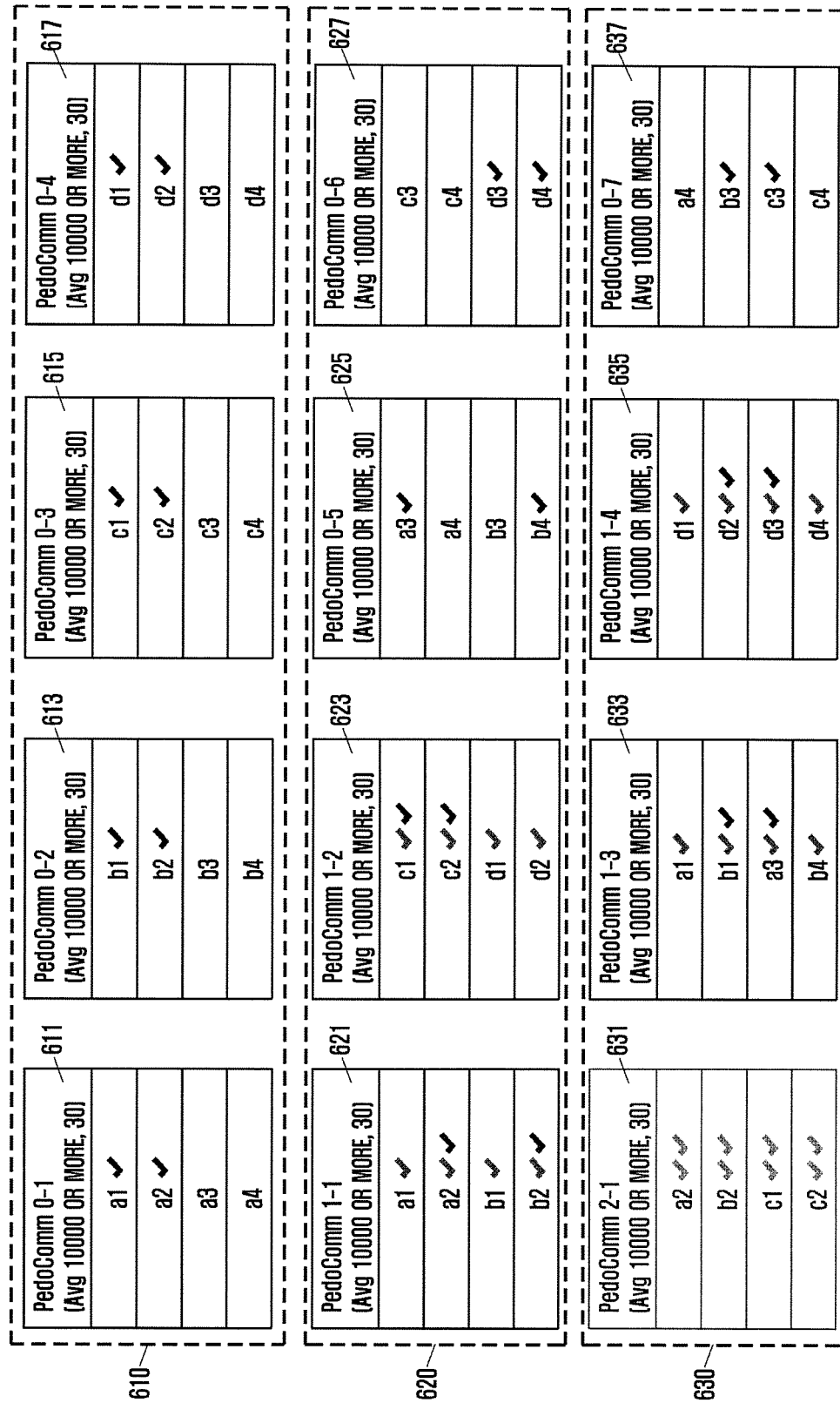
FIGS. 6A and 6B illustrate the league generation by the host device based on conditions according to various embodiments of the present disclosure.

FIG. 6A illustrates the league generation by the host device 400 based on conditions according to various embodiments of the present disclosure.

Figure 6B:
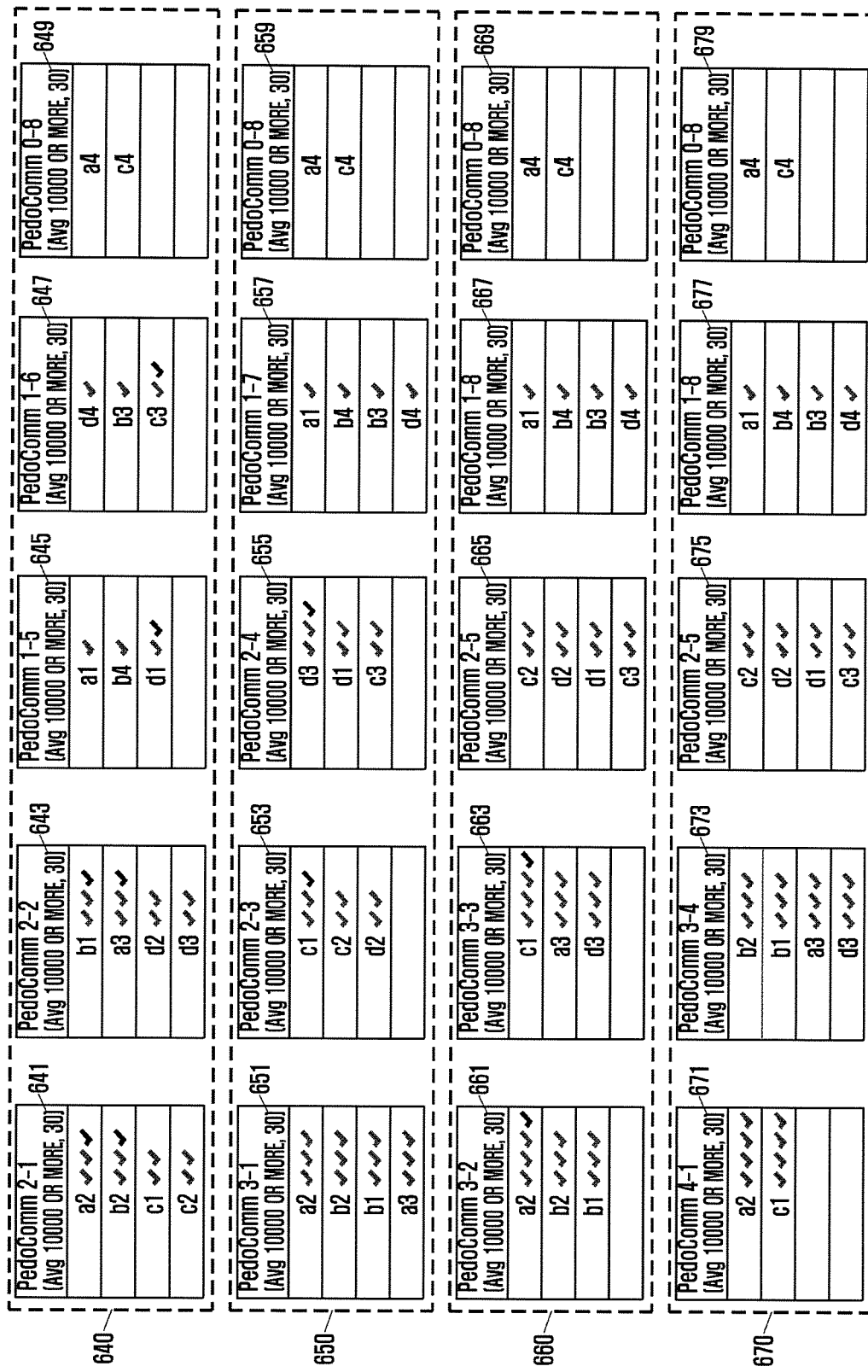

The host device 400 according to an embodiment may generate a group requiring particular conditions. The host device 400 may provide a service using a league service when there are two or more groups. Referring to FIGS. 6A and 6B, a1 to a4, b1 to b4, c1 to c4, and d1 to d4 may be IDs corresponding to electronic devices included in each group. The ID may be changed by the host device 400 and may be determined to correspond to each electronic device by a random function.

Referring to FIG. 6A, the host device 400 may generate a group which requires conditions of 10000 steps or more per week and 30 people or more. A league service may be provided using the generated groups.

A preset first league 610 may include a first group 611, a second group 613, a third group 615, and a fourth group 617. Each group may require the same conditions of 10000 steps or more per week and 30 people or more.

When a preset period (for example, 7 days) elapses, electronic devices, which meet the preset conditions, may be identified in each of the groups included in the first league 610. Devices a1 and a2 may meet the conditions in the first group 611, and devices b1 and b2 may meet the conditions in the second group 613. Devices c1 and c2 may meet the conditions in the third group 615, and devices d1 and d2 may meet the conditions in the fourth group 617.

Groups included in a second league 620 and a configuration of electronic devices may be renewed according to whether the electronic devices included in each of the groups of the first league 610 meet the conditions.

The second league 620 may include a fifth group 621, a sixth group 623, a seventh group 625, and an eighth group 627. The fifth group 621 may include devices a1, a2, b1, and b2 which meet the preset conditions of 10000 steps or more per week during the first league 610. The sixth group 623 may include devices c1, c3, d1, and d2 which meet the conditions in the first league 610. As the fifth group 621 and the sixth group 623 according to an embodiment meet the conditions in the first league 610, text such as 1-1 or 1-2 may be marked in title information.

The seventh group 625 may include devices a3, a4, b3, and b5 which do not meet the preset conditions of 10000 steps or more per week during the first league 610. The eighth group 627 may include devices c3, c4, d3, and d4 which do not meet the preset conditions of 10000 steps or more per week. As the seventh group 625 and the eighth group 627 according to an embodiment do not meet the conditions in the first league 610, text such as 0-5 or 0-6 may be marked in title information.

Groups included in a third league 630 and a configuration of electronic devices may be renewed according to whether the electronic devices included in each of the groups of the second league 620 meet the conditions.

The third league 630 may include a ninth group 631, a tenth group 633, an eleventh group 635, and a twelfth group 637. The ninth group 631 may include devices a2, b2, c1, and c2 which meet the preset conditions of 10000 steps or more during the second league 620. As the ninth group 631 according to an embodiment meets the conditions two times, text of 2-1 may be marked. As the electronic devices included in the ninth group 631 according to an embodiment meet the preset conditions, the renewal may not be performed for a preset period of the third league 630.

The tenth group 633 may include electronic devices which meet the conditions one time until the second league 620. The tenth group 633 may include devices a1, b1, a3, and b4 which meet the conditions one time. The eleventh group 635 may include devices d1, d2, d3, and d4 which meet the conditions of the second league 620 one time. Text data 1-3 and 1-4 indicating that the conditions are met one time may be marked in the tenth group 633 and the eleventh group 635.

The twelfth group 637 may include electronic devices a4, b3, c3, and c4 which do not meet the conditions until the second league 620. Text 0-7 indicating that the conditions are not met may be marked in the twelfth group 637.

FIG. 6B illustrates the league generation by the host device 400 based on conditions according to various embodiments of the present disclosure.

Groups included in a fourth league 640 and a configuration of electronic devices may be renewed according to whether the electronic devices included in each of the groups of the third league 630 meet the conditions.

The fourth league 640 may include a thirteenth group 641, a fourteenth group 643, a fifteenth group 645, a sixteenth group 647, and a seventeenth group 649. The thirteenth group 641 may remain in the configuration of the electronic devices included in the ninth group 631 as the electronic devices included in the ninth group 631 meet all conditions during the third league 630. The thirteenth group 641 may include the same devices a2, b2, c1, and c2 as those of the ninth group 631. As the thirteenth group 641 according to an embodiment meets the conditions two times, text of 2-1 may be marked.

The fourteenth group 643 may include devices b1, a3, d2, and d3 which meet the conditions two times until the third league 630. As the fourteenth group 643 according to an embodiment meets the conditions two times, text of 2-2 may be marked.

The fifteenth group 645 may include electronic devices which meet the conditions one time until the third league 630. The fifteenth group 645 may include devices a1, b1, a3, and b4 which meet the conditions one time. The sixteenth group 647 may include devices d4, b3, and c3 which meet the conditions of the third league 630 one time. Text data 1-5 and 1-6 indicating that the conditions are met one time may be marked in the fifteenth group 645 and the sixteenth group 647, respectively.

The seventeenth group 649 may include electronic devices a4 and c4 which do not meet the conditions until the third league 630. Text 0-8 indicating that the conditions are not met may be marked in the sixteenth group 649. The host device 400 according to an embodiment may determine that the sixteenth group 649 does not meet the preset number of times (for example, does not meet the conditions corresponding to two times) and delete the sixteenth group 649.

Groups included in a fifth league 650 and a configuration of electronic devices may be renewed according to whether the electronic devices included in each of the groups of the fourth league 640 meet the conditions.

The fifth league 650 may include an eighteenth group 651, a nineteenth group 653, a twentieth group 655, a twenty-first group 657, and a twenty-second group 649. The eighteenth group 654 may include electronic devices a2, b2, b1, and a3 based on a result of whether the conditions of the fourth league 640 are met. As the eighteenth group 651 according to an embodiment meets the conditions three times, text 3-1 may be marked.

The nineteenth group 653 may include devices c1, c2, d2, and d2 which meet the conditions two times until the fourth league 640. As the nineteenth group 653 according to an embodiment meets the conditions two times, text 2-3 may be marked. The twentieth group 655 may include electronic devices which meet the conditions two times until the fourth league 640. The twentieth group 655 may include devices c2, d2, d1, and c3 which meet the conditions two times. Text data 2-3 and 2-4 indicating that the conditions are met two times may be marked in the nineteenth group 653 and the twentieth group 655, respectively.

The twenty-first group 657 may include electronic devices a1, b4, b3, and d4 which meet the conditions one time until the fourth league 640. Text data 1-7 indicating that the conditions are met one time may be marked in the twenty first group 657.

The twenty-second group 659 may include electronic devices a4 and c4 which do not meet the conditions until the fourth league 640. Text data 0-8 indicating that the conditions are not met may be marked in the twenty-second group 659. The host device 400 according to an embodiment may determine that the twenty-second group 659 does not meet the preset number of times (for example, does not meet the conditions corresponding to two times) and delete the twenty-second group 659.

Groups included in a sixth league 660 and a configuration of electronic devices may be renewed according to whether the electronic devices included in each of the groups of the fifth league 650 meet the conditions.

The sixth league 660 may include a twenty-third group 661, a twenty-fourth group 663, a twenty-fifth group 665, a twenty-sixth group 667, and a twenty-seventh group 669. The twenty-third group 661 may include electronic devices a2, b2, and b1 based on a result of whether the conditions of the fifth league 650 are met. As the twenty-third group 661 according to an embodiment meets the conditions three times, text 3-2 may be marked. The twenty-fourth group 663 may include electronic devices c1, a3, and d3 based on a result of whether the conditions of the fifth league 650 are met. As the twenty-fourth group 663 according to an embodiment meets the conditions three times, text 3-3 may be marked.

The twenty-fifth group 665 may include devices c2, d2, d1, and c3 which meet the conditions two times until the fifth league 650. As the twenty-fifth group 665 according to an embodiment meets the conditions two times, text of 2-5 may be marked.

The twenty-sixth group 667 may include electronic devices which meet the conditions one time until the fifth league 650. The twenty-sixth group 667 may include devices a1, b4, b3, and d4 which meet the conditions one time. Text data 1-8 indicating that the conditions are met one time may be marked in the twenty-sixth group 667.

The twenty-seventh group 669 may include electronic devices a4 and c4 which do not meet the conditions until the fifth league 650. Text data 0-8 indicating that the conditions are not met may be marked in the twenty-seventh group 669. The host device 400 according to an embodiment may determine that the twenty-seventh group 669 does not meet the preset number of times (for example, does not meet the conditions corresponding to two times) and delete the twenty-seventh group 669.

When a seventh league 670 starts, if groups 671, 673, 675, 677, and 679 included in the seventh league 670 have different numbers of times by which the conditions are met, the host device 400 may end the league. For example, a twenty-eighth group 670 may meet the conditions four times and a twenty-ninth group 673 may meet the conditions three times. A thirtieth group 375 may meet the conditions two times and a thirty-first group 677 may meet the conditions one time. A thirty-second group 679 may meet the conditions zero times.

The host device 400 according to an embodiment may control the electronic devices included in each group to use a friend service when the league ends. For example, the host device 400 may control the electronic devices a2 and c1 included in the twenty-eighth group 671 to use a service for sharing particular information.

Figure 7:
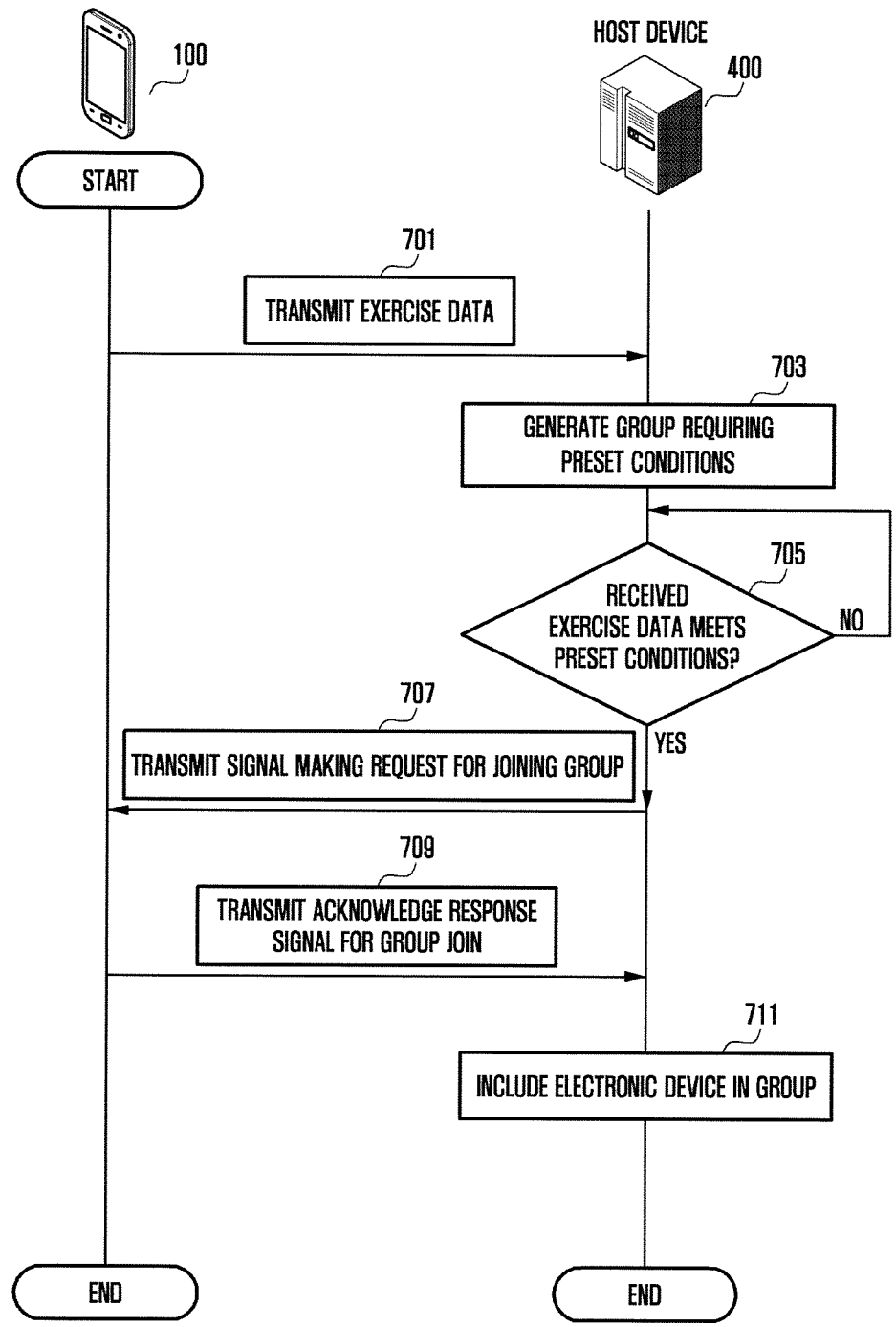
FIG. 7 illustrates an operation for generating a group between the electronic device and the host device according to various embodiments of the present disclosure.

FIG. 7 illustrates an operation for generating a group between the electronic device 100 and the host device 400 according to various embodiments of the present disclosure.

The electronic device 100 may transmit exercise data to the host device 400 in operation 701. Another electronic device may transmit exercise data measured by the electronic device 100, exercise data measured by another electronic device (for example, a wearable device), and exercise data included in another application to the host device 400.

The host device 400 may generate a group which requires preset conditions in operation 703. The preset conditions may be the type of measurement device, gender, the number of people, data on the number of steps, calorie data, and an obesity rate.

The host device 400 determines whether received exercise data meets the preset conditions in operation 705.

The host device 400 transmits a signal making a request for joining the group to the electronic device 100 in operation 707. When the condition corresponding to the number of people of the electronic devices included in the group is met among the preset conditions, the host device 400 according to an embodiment may transmit the signal making a request for joining the group to the electronic devices included in the group.

The electronic device 100 transmits an acknowledge response signal indicating the group join to the host device 400 in operation 709. The host device 400 includes the electronic device 100 in the group in operation 711. When the host device 400 receives a rejection signal indicating no group join, the host device 400 may transmit the signal making a request for joining the group to another electronic device which meets the preset conditions of the group.

Figure 8:
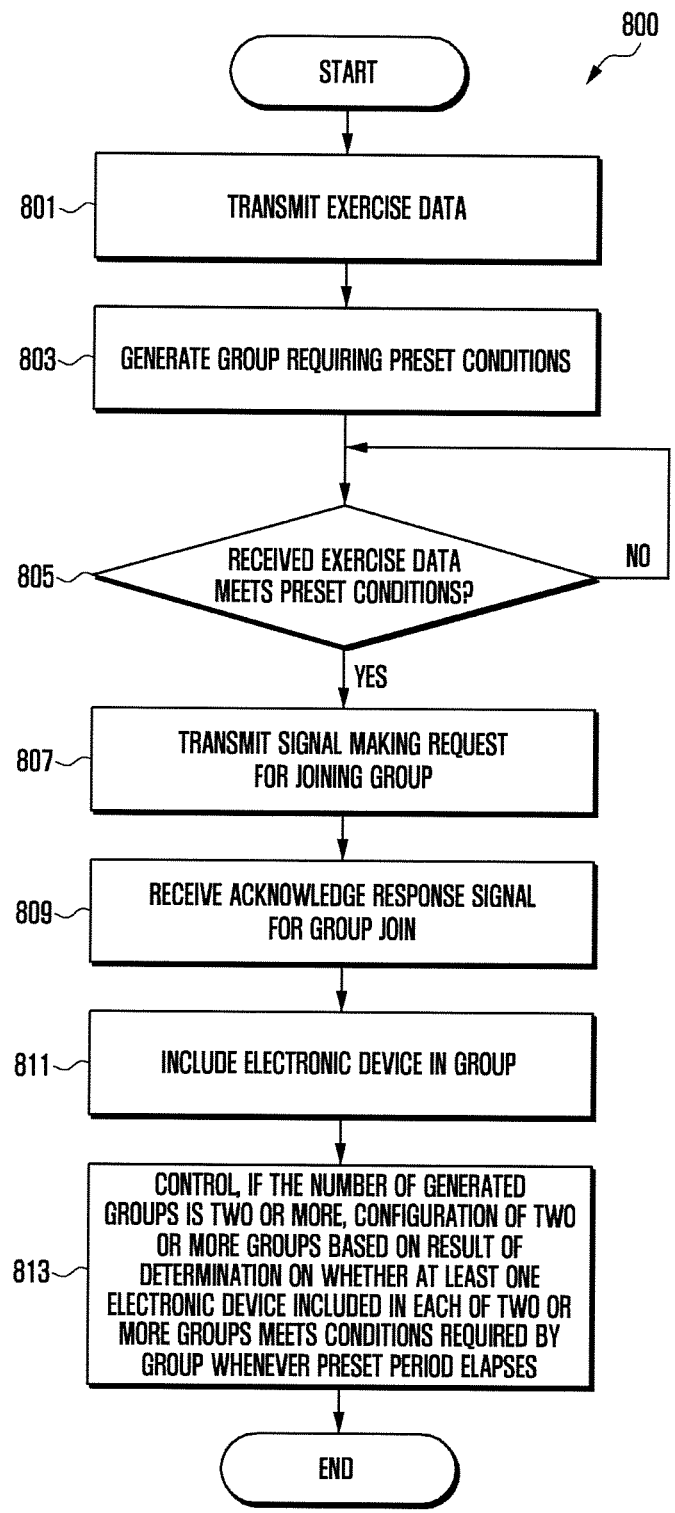
FIG. 8 illustrates a process for generating a group by the host device according to various embodiments of the present disclosure.

FIG. 8 illustrates a process 800 for generating a group by the host device 400 according to various embodiments of the present disclosure.

The host device 400 receives exercise data from the electronic device 100 in operation 801. The exercise data may be exercise data measured by the electronic device 100, exercise data measured by another electronic device (for example, a wearable device), or exercise data included in another application.

The host device 400 may generate a group which requires preset conditions in operation 803. The preset conditions may be the type of measurement device, gender, the number of people, data on the number of steps, calorie data, and an obesity rate.

The host device 400 according to an embodiment may calculate the exercise data received from the electronic device 100 based on a pre-stored calculation method. The host device 400 determines whether received exercise data meets the preset conditions in operation 805.

The host device 400 transmits a signal making a request for joining the group in operation 807. When the condition corresponding to the number of people of the electronic devices included in the group among the preset conditions is met, the host device 400 according to an embodiment may transmit the signal making a request for joining the group to the electronic devices included in the group.

The host device 400 receives an acknowledge response signal indicating the group join in operation 809. The host device 400 includes the electronic device in the group in operation 811. When the host device 400 according to an embodiment receives a rejection signal indicating no group join, the host device 400 may transmit the signal making a request for joining the group to another electronic device which meets the conditions.

When the number of generated groups is two or more, the host device 400 may control the configuration of the two or more groups based on a result of the determination on whether at least one electronic device included in each of the two or more groups meets the conditions required by the group whenever a preset period elapses in operation 813.

When the preset period elapses, the host device 400 according to an embodiment may renew a group to include the electronic device 100 based on a result of the determination on whether the electronic device 100 included in one of the two or more groups meets the conditions required by the group.

When the preset period elapses, the host device 400 according to an embodiment may classify the two or more groups according to whether the conditions required by the groups are met.

The host device 400 according to an embodiment may identify the group, which does not reach the number of times by which the preset conditions are met, among the classified groups. The host device 400 may delete the identified group.

When pieces of information on the number of times by which the conditions required by respective groups of the classified groups are met are different from each other, the host device 400 according to an embodiment may end the controlling of the configuration of the group. The host device 400 may allow the electronic devices included in each group to use a friend service when the configuration of the group ends.

When the preset period elapses, if all electronic devices included in the group meet the conditions required by the group, the host device 400 according to an embodiment may not control the configuration of the group which meets the conditions for the preset period.

The above described components of the electronic device according to various embodiments of the present disclosure may be formed of one or more components, and a name of a corresponding component element may be changed based on the type of electronic device. The electronic device according to the present disclosure may include one or more of the aforementioned components or may further include other additional components, or some of the aforementioned components may be omitted. Further, some of the components of the electronic device according to the various embodiments of the present disclosure may be combined to form a single entity, and thus, may equivalently execute functions of the corresponding elements prior to the combination.

The "module" used in various embodiments of the present disclosure may refer to, for example, a "unit" including one of hardware, software, and firmware, or a combination of two or more of the hardware, software, and firmware. The "module" may be interchangeable with a term, such as a unit, a logic, a logical block, a component, or a circuit. The module may be a minimum unit of an integrated component element or a part thereof. The "module" may be the smallest unit that performs one or more functions or a part thereof. The module may be mechanically or electronically implemented. For example, the "module" according to various embodiments of the present disclosure may include at least one of an Application-Specific Integrated Circuit (ASIC) chip, a Field-Programmable Gate Arrays (FPGAs), and a programmable-logic device for performing operations.

According to various embodiments, at least a part of a device (for example, modules or functions thereof) or a method (for example, operations) according to the various embodiments of the present disclosure may be embodied by, for example, a command stored in a computer readable storage medium in a form of a programming module. When the instruction is performed by at least one processor (for example, the processor 160), the at least one processor may perform a function corresponding to the instruction. The computer-readable storage medium may, for example, be the storage module 120. At least some of the programming modules may be implemented (for example, executed) by, for example, the processor 160. At least a part of the programming module may, for example, include a module, a program, a routine, a set of instructions, or a process for performing at least one function.

The computer readable recording medium may include magnetic media such as a hard disc, a floppy disc, and a magnetic tape, optical media such as a compact disc read only memory (CD-ROM) and a digital versatile disc (DVD), magneto-optical media such as a floptical disk, and hardware devices specifically configured to store and execute program commands, such as a read only memory (ROM), a random access memory (RAM), and a flash memory. In addition, the program instructions may include high class language codes, which can be executed in a computer by using an interpreter, as well as machine codes made by a compiler. The aforementioned hardware device may be configured to operate as one or more software modules in order to perform the operation of various embodiments of the present disclosure, and vice versa.

A module or a programming module according to the present disclosure may include at least one of the described component elements, a few of the component elements may be omitted, or additional component elements may be included. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

Although the present disclosure has been described with embodiments, various changes and modifications may be suggested to one skilled in the art. It is intended that the present disclosure encompass such changes and modifications as fall within the scope of the appended claims.

What is claimed is:

1. A host device comprising:
a transmitter;
a receiver; and
a processor configured to:
receive, at a data management module of the processor, exercise data from an electronic device;
generate, at a group management module of the processor, a group requiring preset conditions;
determine, at the group management module, to include the electronic device in the group based on a determination that the exercise data of the electronic device received from the data management module meets the preset conditions;
transmit, via the transmitter, a signal making a request for joining the group to the electronic device upon determining that the exercise data of the electronic device meets the preset conditions;
include, at the group management module, the electronic device in the group upon receiving, via the receiver, an acknowledge response signal from the electronic device in response to the signal transmitted to the electronic device, the acknowledge response signal indicating that the electronic device will join the group;
in response to generation of at least two groups requiring the same conditions as the preset conditions, generate, at a league management module of the processor, a league service including the at least two groups; and
control, at the league management module, a configuration of the at least two groups included in the league service based on a result of a determination on whether one or more electronic devices included in each of the at least two groups meet the preset conditions required by the group each time a preset period elapses,
wherein the processor is further configured to:
classify, at the league management module, in response to the preset period having elapsed, the at least two groups included in the league service according to whether the preset conditions are met;
receive, at the league management module, in response to the preset period having elapsed, new exercise data from the electronic device; and
determine, at the league management module, based on whether the received new exercise data meets the preset conditions, a specific group to include the electronic device among the classified at least two groups.

2. The host device of claim 1, wherein the processor is further configured to:
calculate, at the data management module, the exercise data received from the electronic device based on a calculation method pre-stored in the host device, and
transmit the calculated exercise data to the group management module.

3. The host device of claim 1, wherein the processor is configured to transmit, via the transmitter, information regarding the specific group to the electronic device in response to determining the specific group.

4. The host device of claim 1, wherein the processor is further configured to:
identify, at the league management module, a group having a number of times by which the preset conditions are met that is equal to or smaller than the preset conditions from among the classified at least two groups, and
delete, at the league management module, the identified group.

5. The host device of claim 1, wherein the processor is further configured to end, at the league management module, controlling of the configuration of the groups when the classified at least two groups have different numbers of times by which the preset conditions required by the groups are met.

6. The host device of claim 1, wherein the processor is further configured to, at the league management module, when the preset period elapses, upon a determination that all electronic devices included in the group meet the preset conditions required by the group, not control a configuration of a group which meets the preset conditions for the preset period.

7. The host device of claim 1, wherein the preset conditions include at least one of data on a number of steps, burnt calorie data, age data, gender data, and type data on the electronic device measuring the exercise data.

8. A method of generating a group by a host device, the method comprising:
receiving, by a data management module, exercise data from an electronic device;
generating, by a group management module, a group requiring preset conditions;
determining, by the group management module, whether to include the electronic device in the group based on whether the exercise data of the electronic device received from the data management module meets the preset conditions;
transmitting, by a transmitter, a signal making a request for joining the group to the electronic device upon determining that the exercise data of the electronic device meets the preset conditions;
including the electronic device in the group when an acknowledge response signal is received, by a receiver, from the electronic device in response to the signal transmitted to the electronic device, the acknowledge response signal indicating that the electronic device will join the group;
in response to generation of at least two groups requiring the same conditions as the preset conditions, generating, by a league management module, a league service including the at least two groups; and
controlling, by the group management module, a configuration of the at least two groups included in the league service based on a result of a determination on whether one or more electronic devices included in each of the at least two groups meet the preset conditions required by the group each time a preset period elapses,
wherein the controlling the configuration further comprises:
classifying, in response to the preset period having elapsed, the at least two groups included in the league service according to whether the preset conditions are met;
receiving, in response the preset period having elapsed, new exercise data from the electronic device; and
determining, based on whether the received new exercise data meets the preset conditions, a specific group to include the electronic device among the classified at least two groups.

9. The method of claim 8, further comprising calculating, by the data management module, the exercise data received from the electronic device based on a calculation method pre-stored in the host device and transmitting the calculated exercise data to the group management module.

10. The method of claim 8, further comprising: transmitting information regarding the specific group to the electronic device in response to determining the specific group.

11. The method of claim 8, further comprising:
identifying, by the league management module, a group having a number of times by which the preset conditions are met that is equal to or smaller than the preset conditions from among the classified at least two groups; and
deleting, by the league management module, the identified group.

12. The method of claim 8, further comprising: when the classified at least two groups have different numbers of times by which the preset conditions required by the at least two groups are met, ending controlling of the configuration of the at least two groups.

13. The method of claim 8, further comprising: when the preset period elapses upon a determining that all electronic devices included in the group meet the preset conditions required by the group, not controlling a configuration of a group that meets the preset conditions for the preset period.

14. The method of claim 8, wherein the preset conditions include at least one of data on a number of steps, burnt calorie data, age data, gender data, and type data on the electronic device measuring the exercise data.

15. A system comprising:
a transmitter;
a receiver; and
a host device including a processor configured to:
receive, at a data management module of the processor, exercise data from an electronic device;
generate, at a group management module of the processor, a group requiring preset conditions;
determine, at the group management module, to include the electronic device in the group based on a determination that the exercise data of the electronic device received from the data management module meets the preset conditions;
transmit, via the transmitter, a signal making a request for joining the group to the electronic device upon determining that the exercise data of the electronic device meets the preset conditions;
include, at the group management module, the electronic device in the group upon receiving, via the receiver, an acknowledge response signal from the electronic device in response to the signal transmitted to the electronic device, the acknowledge response signal indicating that the electronic device will join the group;
in response to generation of at least two groups requiring the same conditions as the preset conditions, generate, at a league management module of the processor, a league service including the at least two groups; and
control, at the league management module, a configuration of the at least two groups included in the league service based on a result of a determination on whether one or more electronic devices included in each of the at least two groups meet the preset conditions required by the group each time a preset period elapses, wherein the processor is further configured to:
classify, at the league management module, in response to the preset period having elapsed, the at least two groups included in the league service according to whether the preset conditions are met;
receive, at the league management module, in response to the preset period having elapsed, new exercise data from the electronic device; and
determine, at the league management module, based on whether the received new exercise data meets the preset conditions, a specific group to include the electronic device among the classified at least two groups.

16. The system of claim 15, wherein the processor is further configured to not include the electronic device in the group based on a determination, at the group management module, that the exercise data received from the data management module fails to meet the preset conditions.

* * * * *